United States Patent [19]
Jensen

[11] Patent Number: 4,759,363
[45] Date of Patent: Jul. 26, 1988

[54] SCALPEL WITH REMOVABLE DEPTH GUARD

[76] Inventor: Ronald P. Jensen, 1612 Golf Club Dr., Glendale, Calif. 91206

[21] Appl. No.: 776,851

[22] Filed: Sep. 17, 1985

[51] Int. Cl.⁴ .............................................. A61F 17/32
[52] U.S. Cl. .................................... 128/305; 128/317; 30/293
[58] Field of Search ................. 30/293, 294, 289, 300; 128/305, 317

[56] References Cited

U.S. PATENT DOCUMENTS

| | | | |
|---|---|---|---|
| 3,457,643 | 7/1969 | Hill | 30/293 |
| 3,945,117 | 3/1976 | Beaver | 30/289 X |
| 4,073,056 | 2/1978 | Schaeffer et al. | 30/289 X |
| 4,324,044 | 4/1982 | Shahinian | 30/294 |
| 4,473,076 | 9/1984 | Williams et al. | 30/320 X |
| 4,499,898 | 2/1985 | Knepshield | 30/320 X |
| 4,516,575 | 5/1985 | Gerhard et al. | 128/305 |
| 4,520,815 | 6/1985 | Marinoff | 128/305 X |
| 4,534,348 | 8/1985 | Fedorov et al. | 30/320 X |
| 4,552,146 | 11/1985 | Jensen et al. | 30/293 X |
| 4,569,133 | 2/1986 | Schmidt | 30/293 |

FOREIGN PATENT DOCUMENTS

| | | | |
|---|---|---|---|
| 2487188 | 1/1982 | France | 128/305 |
| 8200759 | 3/1982 | PCT Int'l Appl. | 128/305 |
| 218942 | 7/1924 | United Kingdom | 128/317 |
| 2113550A | 8/1983 | United Kingdom | 128/305 |

Primary Examiner—Ira S. Lazarus
Assistant Examiner—Richard R. Cole
Attorney, Agent, or Firm—Nilsson, Robbins, Dalgarn, Berliner, Carson & Wurst

[57] ABSTRACT

A scalpel is set forth having a handle with a blade at one end which defines a first depth of cut. To transform the scalpel for cutting to a lesser, second depth of cut a removable guard is provided. The guard is attached to the scalpel handle with a bayonet-type connection and has a tip to be disposed near one side of the blade. When the guard is attached, the blade projects past the tip a predetermined amount to define the second depth of cut. Guards are constructed for right or left hand preference.

17 Claims, 2 Drawing Sheets

SCALPEL WITH REMOVABLE DEPTH GUARD

FIELD OF THE INVENTION

This invention relates to surgical scalpels and more particularly to scalpels adapted for surgeries where precise incisions are desired or required such as cataract surgery, plastic surgery, vascular surgery, orthopedic surgery or the like.

BACKGROUND OF THE INVENTION

In certain surgical procedures, it is often highly desirable that smooth, precise, continuous incisions of a controlled depth be made. Irregular or discontinuous incisions may result in complications in healing and cause an irregular and perhaps enlarged scar. An imprecise incision may result in wound leakage or, in particular, in cataract surgery, in astigmatism.

With particular reference to cataract surgery, an initial incision is required at the sclera of the eye adjacent the cornea, the incised tissue being retracted to gain access to the lens of the eye. This incision is typically made along an arc following the curvature of the cornea. According to the prior art, the surgeon would by hand make an initial incision groove and following the groove, a subsequent intraocular incision to gain access to the lens.

The tissue of the sclera being incised typically has a thickness of between 300–700 microns. To limit the depth of cut, various scalpels have been devised as described in U.S. application Ser. No. 567,263 filed Dec. 30, 1983 now U.S. Pat. No. 4,552,146 and entitled "Disposable Ophthalmic Instrument for Performing Radial Keratotomy on the Cornea." The scalpel according to this application is adapted, using external gauges or the like, to have a selected depth of cut.

Cutting initially to the required depth, i.e., to incise the sclera, may result in an irregular or perhaps imprecise cut due to the resistance of the relatively large amount of tissue being incised and the fact that the incision is being made by hand. It would be advantageous, if an initial incision in the sclera of a nominal depth could first be made by the surgeon, the initial incision defining a line for the ultimate, complete incision to be made. To provide for a regular closure of the incision and to prevent wound leakage and astigmatism, the final incision is made at an angle (beveled). Using this initial, nominal depth incision, the surgeon could then retrace the incision cutting to the desired depth, the initial incision acting as a guide.

Given the problem and the desired solution, the applicant has achieved desired results by using a pair of scalpels. A first scalpel, having a preset nominal depth of cut, was used to make the initial incision. In that a relatively shallow depth cut was being made a smooth, precise and continuous initial incision could be made. Thereafter, a second scalpel having a deeper depth of cut was inserted into the initial incision and, using that initial incision as a guide, was positioned at the correct cutting angle and was moved to retrace the initial incision and complete the intraocular incision. The smooth, precise and continuous incision defined by this procedure has been found advantageous in that the incision when closed by suturing forms a watertight closure and prevents astigmatism.

Of course, it is to be understood that this procedure could apply equally well to surgeries other than those involved with the eye, such as cosmetic or other surgeries involving the skin where precise wound closure is necessary.

The use of two or more scalpels, one set to have a preset depth of cut, is costly since the scalpels are usually discarded. Further, the use of a pair of scalpels may be time consuming and frustrating to the surgeon since the surgeon must change from the first to the second scalpel.

SUMMARY OF THE INVENTION

There is, therefore, provided in the practice of the present invention a scalpel which is transformable via a removable guard, between a condition at which it is adapted to make an initial incision to a predetermined, nominal first depth to a second condition at which it is adapted to make an incision to a greater second depth to complete the incision. For surgical techniques using cataract surgery as an example, only one scalpel need be used and hence a cost savings can be realized. Further, the smooth, continuous and precise incision made by the scalpel promotes success of the procedure. Of course, the scalpel according to the present invention has applications to other surgical techniques other than those involved with the eye.

Toward this end the scalpel, according to the present invention, includes a handle having at one end a cutting blade, which may or may not have a predetermined, fixed depth of cut. For cataract surgery, the blade is disposed on the handle such that its depth of cut is greater than the thickness of the scleral tissue. The scalpel also includes a guard having a tip and means for quickly and detachably coupling the guard to the handle. The coupling means includes means for locating the guard at a predetermined position on the handle whereat the tip is disposed proximate the blade and the blade projects past the tip a predetermined amount defining a nominal depth of cut for the initial incision. With the guard on the handle, the surgeon makes the initial incision to a nominal depth predetermined by the relationship between the guard tip and the blade. After the initial incision has been completed, the surgeon quickly and easily detaches the guard, reinserts the cutting blade into the initial incision and retraces the initial incision completing the cut to the required depth.

In the preferred embodiment, the coupling means includes a rectangular key disposed on the handle near the tip, the key preferably aligned with the blade to aid the surgeon's grasp of the handle and for aligning the blade in the hand by simply feeling the location of the key. The coupling means further includes a slot disposed on the guard to receive the key as the guard is inserted over the handle one end. Once the guard has been disposed over the handle one end it is rotated to precisely locate the key in a pocket firmly coupling the guard to the handle and precisely locating its tip relative to the blade. The key and pocket are precisely positioned during the manufacture thereof so that a predetermined relative position between the guard tip and blade is had when the guard is coupled to the handle.

The guard may be fashioned to include a sleeve having the aforementioned slot and pocket and a projecting arm the end of which defines the tip. During the initial incision, the scalpel is held by the surgeon such that the tip does not obstruct the surgeon's view of the initial incision being made. That is, during the initial incision the surgeon views the penetration of the tissue by the blade and the guard is disposed at the side of the blade out of the line of view. For right-handed surgeons, where, for example, the sclera of the eye above the cornea is being cut in a counterclockwise direction, it is advantageous to locate the tip to one side of the blade whereas a left-handed surgeon would make the incision in a clockwise fashion and accordingly the tip should be disposed at the other side of the blade. For this purpose, the scalpel according to the present invention includes a set of guards having those adapted, when positioned on the handle, locate the tip to the one side of the blade and guards adapted to locate the tip to the other side of the blade. Color coding of the guards is employed to aid the surgeon in selection.

BRIEF DESCRIPTION OF THE DRAWINGS

These and other features and advantages of the present invention will become apparent as the same becomes better understood with reference to the specification, claims and drawings wherein:

DETAILED DESCRIPTION

Figure 1A:
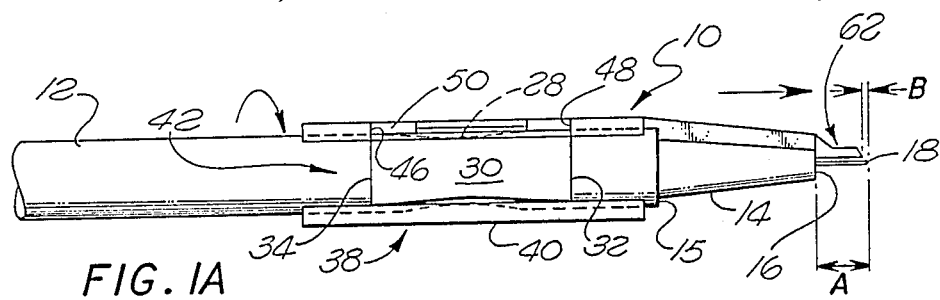
FIG. 1A is a top view of a scalpel according to the present invention for making incisions from left to right.
Figure 1B:
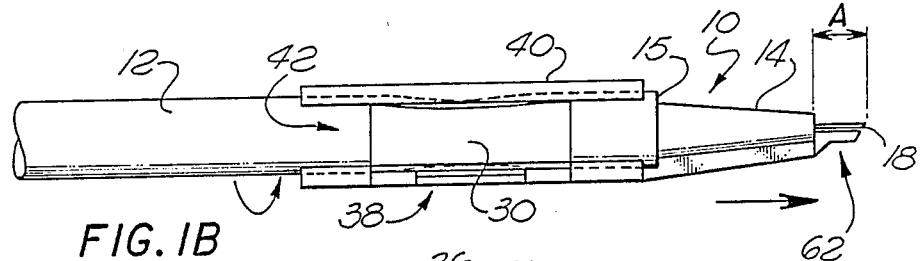
FIG. 1B is the scalpel according to the present invention similar to that of FIG. 1A for making incisions particularly from right to left.

Turning to the drawings, FIGS. 1A and 1B illustrate a scalpel 10 according to the present invention. Scalpel 10 is adapted to make an initial incision of a nominal first depth and is transformable to make an incision of a second, greater depth. The scalpel of FIG. 1A is particularly adapted to make the aforesaid initial incision of nominal depth in a direction from left to right whereas the scalpel of FIG. 1B is adapted to make the initial incision of nominal depth in a direction from right to left. For example, given the relative position of the surgeon's hand to the patient, the scalpel of FIG. 1A may be particularly adapted for use in the right hand whereas the scalpel of FIG. 1B may be adapted for use in the left hand. Dependent upon the surgeon's preference, i.e., right-handedness or left-handedness, the scalpel of FIG. 1A may be preferred by a right-handed surgeon whereas the scalpel of FIG. 1B may be preferred by a left-handed surgeon. Since the embodiments of the scalpel represented by FIGS. 1A and 1B are functionally and structurally similar, the following description will be primarily directed to the embodiment of FIG. 1A.

The scalpel 10 includes a handle 12 having at one end a conical mount 14 which tapers downwardly from the handle 12 to a smaller diameter base 16. An annular rim 15 defines a transition surface between the diameter of the handle and that of the base 16. Secured to the base 16 is a blade 18 of sharpened surgical steel having, as shown FIG. 5, a point 20 for penetrating tissue and a cutting edge 22.

To control the depth of cut of the blade 18, the blade 18 is so positioned and secured to the handle such that the point 20 is at a predetermined distance from the base 16 defining a depth of cut A, as shown in FIGS. 1A and 1B which may or may not be preset to a precise, predetermined depth. For example, when the scalpel 10 is adapted for cataract surgery, depth of cut A may be approximately 1000 microns since the tissue of the sclera being cut typically has a thickness of between 300–700 microns.

During the incision, the blade is inserted through the tissue to complete the intraocular incision.

Figure 3:
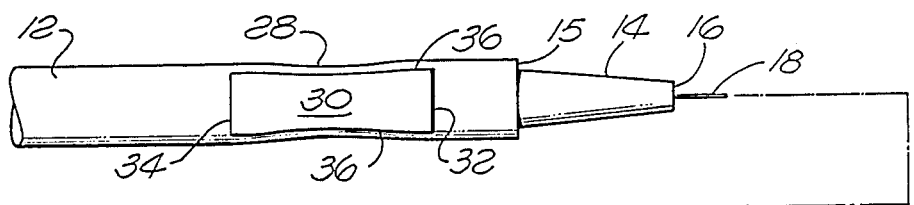
FIG. 3 is a top assembly view of the guard for the scalpel of FIG. 1A.

As best shown in FIG. 3, the handle 12 may include a circumferential indentation 28 to better accommodate the surgeon's grip of the scalpel. Proximate the mount 14 and indentation 28, the handle 12 also includes a rectangular, outwardly projecting key 30. Key 30 includes radial forward and rear walls 32 and 34, respectively, and side walls 36. The key 30 is aligned with respect to the blade 18 so that the surgeon can, by feel of the key 30, determine the orientation of the blade and its edge 22. According to the embodiment shown, the longitudinal axis for the key 30 is aligned with the cutting edge 22. The key 30 also enhances the surgeon's grip of the scalpel and more particularly its handle 12 in that the key 30 may conveniently be gripped between the thumb and the forefinger.

To cooperate with the handle 12 the scalpel 10 further includes a guard 38 and means for coupling the guard 38 with, for example, a bayonet-type connection, to the handle 12 to limit the depth of cut of the blade to a predetermined, lesser depth. As shown in FIG. 1A, this lesser depth of cut is represented by depth B. In certain surgical procedures, such as cataract surgery, it has been found advantageous to make an initial incision at the desired location and along the desired line at a nominal, first depth, represented by depth B which may be 300–400 microns. Since relatively little tissue is being cut a smooth, precise, continuous initial incision can be made by the surgeon.

Figure 5:
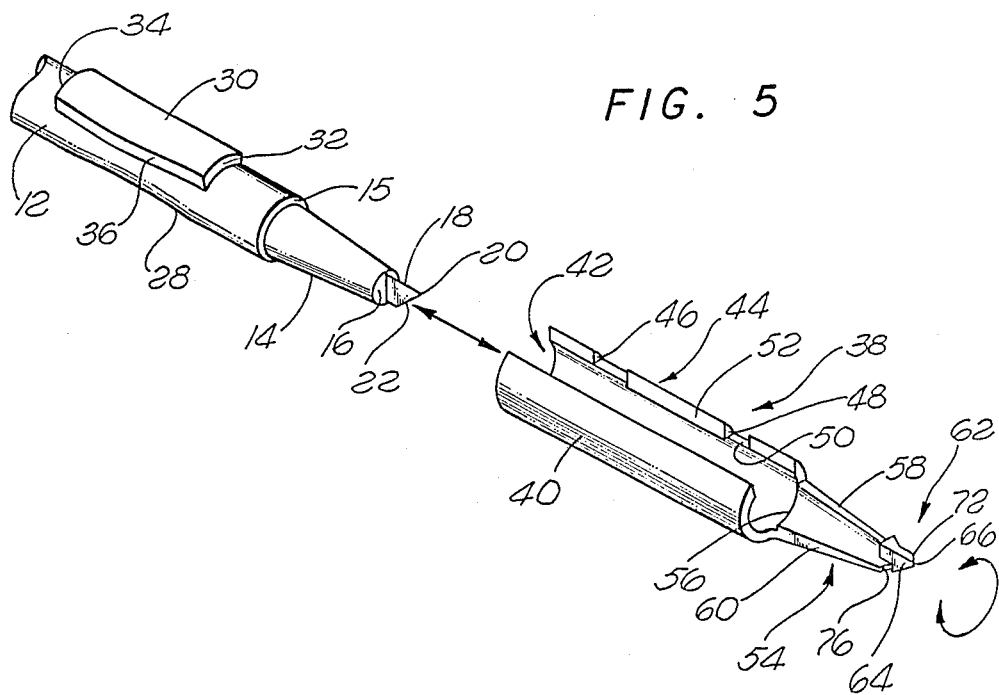
FIG. 5 is a perspective assembly view of the scalpel according to the present invention showing the coupling between the guard and handle.

As shown in the drawings, a bayonet-type connection is provided between the guard 38 and handle 12. The guard 38 includes a sleeve 40 having an inside diameter adapted to closely fit over the handle 12. The sleeve 40 includes a longitudinal extending slot 42 having an arc length slightly greater than that represented by the span between the side walls 36 of the key 30. The guard 38 and more particularly its sleeve 40 can be passed over the handle 12 as shown in FIGS. 3 and 5 with the slot 42 accommodating the key 30. The guard 38 can be fashioned from a plastic, metal or any other suitable materials. When the guard 38 is positioned over the handle 12, the sleeve 40 resiliently expands providing an interference fit between the guard 38 and handle 12 to prevent the guard 38 from inadvertently rotating relative to the handle 12.

As shown in FIGS. 3 and 5, the sleeve 40 also includes a rectangular pocket 44 opening into the slot 42 and defined by first and second walls 46 and 48 and bottom wall 50. The first and second walls 46 and 48 are spaced apart so as to closely receive the key 30 when the guard 38 is passed over the handle 12 and rotated to thereby position at least a portion of the key 30 in the pocket 44. The positioning of the key 30 within the pocket 44 such that the first and second walls 46 and 48 abut the forward and rear walls 32 and 34 to confine the key 30 within the pocket 44 precisely axially positions and firmly holds the guard 38 on the handle 12. A tab 52 projects from the bottom wall 50 to contact a side wall 36 to rotationally limit and align the guard and more particularly the sleeve 40 on the handle 12 for purposes which will hereinafter become evident.

Figure 2:
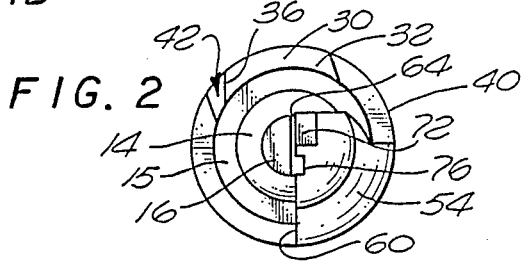
FIG. 2 is an end view of the scalpel according to the present invention.
Figure 4:
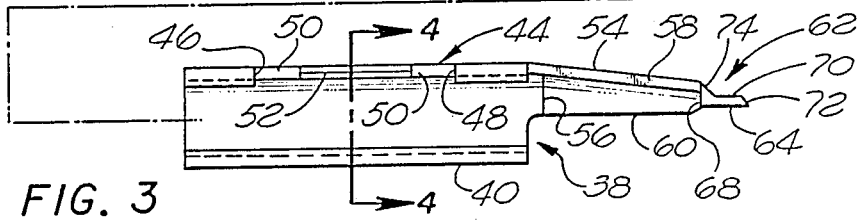
FIG. 4 is a section view of the guard taken along line 4—4 of FIG. 3.
Figure 6:
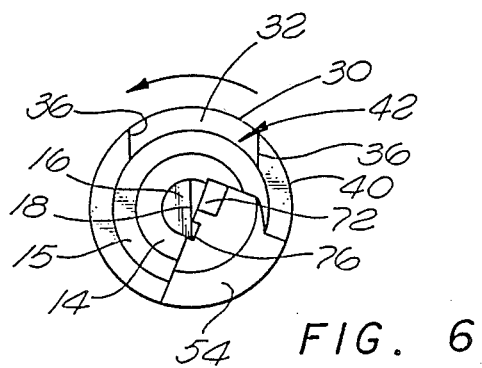
FIG. 6 is an end view of the scalpel of FIG. 1A illustrating the coupling and decoupling of the guard.

Projecting longitudinally from the sleeve 40, the guard 38 further includes an arm 54 which is angled to follow the contour of the conical mount 14 and may be somewhat arcuate in cross-section. At the junction between the arm 54 and sleeve 40, the arm 54 is somewhat thicker than the sleeve 40 to define an arcuate stop 56 adapted to abut the annular rim 15 of the handle 12 when the guard 38 is positioned over the handle 12 to initially limit the axial positioning of the guard on the handle. Arm 54 tapers and thins as it extends outwardly from the stop 56 defining converging side margins 58 and 60 for the arm 54. Remote from the sleeve 40 the side margins terminate at a tip 62. Tip 62 is defined by a face 64 which is adapted to, when the guard 38 is disposed on the handle 10, lie parallel and adjacent the blade 18 and to substantially overshadow the blade 18. As best shown in FIGS. 2 and 4, the face 64 is aligned substantially with side margin 60. The face 64 is somewhat triangular having a truncated apex 66 adapted to be positioned relative to the blade point 20 to define the nominal depth of cut B as illustrated in FIG. 1. To so define the face 64 the tip 62 includes a surface 68 remote from the apex 66 and lying orthogonal to the face 64 fashioning the transition between the arcuate arm 54 and its tip 62. On its outer surface the tip 62 may taper or neck down to define an outer wall 70 for the tip 62 which extends from a rounded end 72 which engages the tissue being severed and intersects the apex 66 to a ridge 74 forming the transition from the outer wall 70 to the surface defined by the arm 54. For purposes which will hereinafter become evident and with reference to FIGS. 2 and 4 through 6, a shallow notch 76 is formed in the face 64 and side margins 60. To position the guard 38 on the handle 10, the guard is aligned with the handle such that the key 30 is positioned to register with the slot 42 of the sleeve 40, as shown in FIG. 5. The guard is passed over the handle 12, the sleeve resiliently expanding a small amount to accommodate the handle 12 and the key 30 passing into the slot 42. When the guard 38 is at the approximate desired axial position the stop 56 engages the rim 15. As shown in FIG. 6, as the guard is initially passed on to the handle 12, the notch 76 accommodates the blade 18 without interference. Thereafter, the guard is rotated in a counterclockwise direction to receive at least a portion of the key 30 within the pocket 44. The tab 52 is constructed to engage by side wall 36 to precisely limit the rotation of the guard 38 the desired amount. In this position, as shown in FIG. 1A, the first wall 46 abuts key rear wall 34 and the second wall 48 abuts key forward wall 32 thereby precisely locating the guard 38 on the handle 12. During manufacture, the first and second walls 46 and 48 and key rear and side walls 34 and 36 are disposed to achieve the desired relative position of the guard 38 on the handle 12. With the guard so positioned, the surgeon can make the initial, nominal incision at depth B along the desired line. Since a relatively small amount of tissue is being cut a smooth, continuous incision can easily be made. Once the initial incision has been made at nominal depth B, the guard 38 is rotated clockwise (FIG. 5) to release the key 30 from the pocket 44 and the guard 38 is removed from the handle 12. The surgeon then, using the initial nominal incision as a guide, inserts the blade 18 at an angle into the nominal incision and using that incision as a guide retraces the cut beveled, completing the intraocular incision.

By this procedure, it can be appreciated that by using the initial cut as a guide a smooth, continuous, intraocular, beveled incision can be made which provides for a watertight closure and reduces astigmatism. Furthermore, the initial cutting at nominal depth and finished incision are accomplished by using one scalpel, thereby achieving a cost savings.

For the scalpel 10 of FIG. 1B, the guard 38 is passed over the handle 12 and is rotated clockwise locking the guard to the handle 12 and its key 30. As illustrated, the guard for this embodiments can be a mirror image of that shown in FIG. 1A for use with the same handle. Guard 38 is rotated counterclockwise for removal from the handle.

To aid surgeons in selecting which guard 38 to select, i.e., the FIG. 1A or FIG 1B embodiment the guards may be color coded. One color for the FIG. 1A embodiment and another color for the FIG. 1B embodiment. Further, the guards can be made to define different depths of cut B as desired.

While I have shown and described certain embodiments of the present invention, it is to be understood that it is subject to many modifications without departing from the spirit and scope of the claims as set forth herein. For example, the key could be disposed on the guard and a cooperative structure such as a J-slot could be fashioned on the handle.

What is claimed is:

1. A scalpel comprising:
   a handle having at one end a mount terminating at a base;
   a blade disposed at the mount and defining a first depth of cut in relation to the base;
   a detachable guard adapted to limit the depth of cut of the blade to a predetermined, lesser second depth of cut when in place, the guard including at one end a face portion adapted to lie parallel to and adjacent a side of the blade and a tip; and
   means for removably attaching the guard to the handle, the attaching means including a connection between the guard and the handle defined by a key and a slot, the key and slot positioned to located the tip in relation to the blade such that the blade projects past the tip a predetermined amount defining the second depth of cut.

2. The scalpel of claim 1 wherein the first depth of cut is fixed at a first, predetermined depth of cut.

3. The scalpel of claim 2 wherein the first predetermined depth of cut is about 3000–5000 microns.

4. The scalpel of claim 2 wherein the predetermined second depth of cut is in the range of 300–400 microns.

5. The scalpel of claim 1 wherein the guard includes a sleeve adapted to pass over the handle and the attaching means includes a key on the handle and a slot in the sleeve, passing of the sleeve over the handle causing the key to register with the slot, said sleeve further including a pocket opening to the slot, rotation of the sleeve locating the key in the slot to locate the guard so that said blade projects past the tip the predetermined second depth of cut.

6. The scalpel of claim 5 wherein the guard includes an arm projecting from the sleeve to the tip disposed adjacent and to one side of the blade.

7. The scalpel of claim 6 wherein the tip includes a notch to accommodate the blade when the sleeve is passed over the handle.

8. A scalpel comprising:
   a handle formed with two opposing ends, with a first end having a cutting blade secured therein to position a cutting edge of the blade at a distance from the handle first end to define a first depth of cut, the handle further being formed with a protuberance at a selected distance from the handle first end; and
   a guard detachable means which is formed to be positioned on the handle, the guard means defining a second depth of cut of the blade when so positioned, and including a securing means which engages said protuberance for retaining the guard means at a position along the handle, the guard means further formed with a) a portion which extends past the handle first end outwards along the cutting blade, b) a face which is adapted to lie parallel to and adjacent a side of the blade, and c) a tip portion which extends for a selected distance from the handle to position the tip portion of the guard means at a distance from the blade cutting edge to define the second depth of cut.

9. The scalpel of claim 8 wherein the key is a rectangular protuberance extending sufficiently that a user can feel its location.

10. The scalpel of claim 4 wherein the rectangular protuberance is longitudinally in line with the blade thereby enabling the surgeon to determine the positioning of the blade by feel of the protuberance.

11. The scalpel of claim 4 wherein the securing means includes a rectangular pocket to closely receive the rectangular protuberance when the guard is positioned along the handle at said predetermined relationship to define the second depth of cut.

12. The scalpel of claim 4 wherein the guard includes a cylindrical sleeve portion adapted to be axially received over the handle one end, the sleeve portion including a longitudinal slot to pass the rectangular protuberance and a rectangular pocket opening to the slot to closely receive the rectangular protuberance and removably couple the guard to the handle at said predetermined relationship upon rotation of the guard relative to said handle.

13. The scalpel of claim 12 wherein the pocket includes a tab to engage the rectangular protuberance when the guard is rotated to precisely limit said rotation.

14. The scalpel of claim 8 wherein the guard includes a sleeve portion adapted to be removably coupled to the handle at a predetermined relative position, an arm projecting from the sleeve portion to a tip disposed at one side of the blade, said blade exposed from the tip defining said second depth of cut.

15. The scalpel of claim 14 wherein said blade is exposed to define a second depth of cut in the range of 300 to 400 microns.

16. A scalpel comprising:
   a handle having at one end a base and a cutting blade, the blade having a point at a predetermined distance from the base to define a first depth of cut, the handle having a substantially radially protruding key;
   a detachable guard means which, when attached to the handle, limits the depth of cut of the blade to a predetermined, lesser second depth of cut, the guard including a face portion adapted to lie parallel to and adjacent a single side of the blade, and a tip; and
   means for detachably coupling the guard to the handle, the coupling means including means for securing the guard to the handle and key at a position on the handle whereby the tip is disposed proximate the blade and the blade projects past the tip an amount defining the lesser second depth of cut by the relationship between the blade and the guard secured to the handle.

17. A scalpel comprising:
   a handle formed with two opposing ends, with a first end having a cutting blade secured therein to position the cutting edge of the blade at a distance from the handle first end to define a first depth of cut, the handle further being formed with a rectangular protuberance longitudinally in line with the blade at a selected distance from the handle first end, the protuberance extending sufficiently that a user can feel its location and determine the position of the blade by feel of the protuberance; and
   a detachable guard means which is formed to be positioned on the handle, the guard means including a securing means which engages the protuberance for retaining the guard means in a position along the handle, the guard means further formed with a portion which extends past the handle first end outwards along the cutting blade for a selected distance to position a first end of the guard means at a distance from the blade cutting edge to define a second depth of cut.

* * * * *